United States Patent
Ghosh et al.

(10) Patent No.: US 10,259,993 B2
(45) Date of Patent: Apr. 16, 2019

(54) STABILIZED ACID PRECURSOR AND ACID-ENZYME FORMULATIONS FOR DRILLING MUD CAKE REMOVAL

(71) Applicant: Epygen Labs FZ LLC, Dubai (AE)

(72) Inventors: Debayan Ghosh, Dubai (AE); Ineeyan Ariyaratnam, Dubai (AE); Punit Bansal, Dubai (AE)

(73) Assignee: EPYGEN LABS FZ LLC, Dubai (AE)

( * ) Notice: Subject to any disclaimer, the term of this patent is extended or adjusted under 35 U.S.C. 154(b) by 373 days.

(21) Appl. No.: 13/863,225

(22) Filed: Apr. 15, 2013

(65) Prior Publication Data

US 2013/0231268 A1 Sep. 5, 2013

(51) Int. Cl.
*C09K 8/86* (2006.01)
*C09K 8/52* (2006.01)
(Continued)

(52) U.S. Cl.
CPC .................. *C09K 8/86* (2013.01); *C09K 8/52* (2013.01); *C12N 9/2414* (2013.01); *C12N 9/96* (2013.01); *C12Y 302/01001* (2013.01)

(58) Field of Classification Search
CPC .... F01D 19/00; F02C 6/08; F02C 7/26; F05D 2260/85
See application file for complete search history.

(56) References Cited

U.S. PATENT DOCUMENTS 4,284,722 A 8/1981 Tamuri et al.
4,617,662 A 10/1986 Auer, Jr. et al.
(Continued)

OTHER PUBLICATIONS

Shaw A, et al, Protein engineering of alpha-amylase for low pH performance, Curr Opin Biotechnol Aug. 10, 1999(4), abstract, 1 page.*

(Continued)

*Primary Examiner* — Alicia Bland
(74) *Attorney, Agent, or Firm* — Leydig, Voit & Mayer, Ltd.

(57) ABSTRACT

Enzyme formulations should stay active and devoid of all possible inactivation processes during transport and long-term storage. The stabilization of enzymatic activity, especially in presence of critical functional components for specialized application, has been a long-standing obstacle when stored over an extended period of time. One such obstacle is the stability of enzyme in presence of weak acids in formulation, which is often desired to efficiently break down biopolymer filtercake embedded in a carbonate matrix, in the open-hole section of a horizontal well, for hydrocarbon production. The invention comprises methods and compositions to enhance the long-term storage stability of an enzyme formulation consisting of an in-situ acid precursor system, where in-situ generated precursors are mainly ester compounds that dissociate by slow hydrolysis to generate organic acid, shifting the pH of the formulation outside the pKa of the enzyme protein. The methods and compositions include the addition of high concentrations of metal halide salts, a pH control additive, and a water activity reducing agent. The methods and compositions of the invention provide a high degree of stability for enzyme formulation at long-term storage conditions.

4 Claims, 5 Drawing Sheets

(51) Int. Cl.
*C12N 9/26* (2006.01)
*C12N 9/96* (2006.01)

(56) References Cited

U.S. PATENT DOCUMENTS

| | | | |
|---|---|---|---|
| 4,682,654 A | | 7/1987 | Carter et al. |
| 5,067,566 A | | 11/1991 | Dawson |
| 5,126,051 A | | 6/1992 | Shell et al. |
| 5,224,544 A | | 7/1993 | Tjon-Joe-Pin et al. |
| 5,441,109 A | | 8/1995 | Gupta et al. |
| 5,510,047 A | * | 4/1996 | Gabriel ............... C11D 3/0094 510/221 |
| 5,547,026 A | | 8/1996 | Brannon et al. |
| 5,566,759 A | | 10/1996 | Tjon-Joe-Pin et al. |
| 5,678,632 A | | 10/1997 | Moses et al. |
| 5,881,813 A | * | 3/1999 | Brannon ............... C09K 8/605 166/304 |
| 6,110,875 A | | 8/2000 | Tjon-Joe-Pin et al. |
| 6,702,023 B1 | | 3/2004 | Harris et al. |
| 6,763,888 B1 | * | 7/2004 | Harris ............... C09K 8/52 166/300 |
| 6,794,340 B2 | | 9/2004 | Nguyen et al. |
| 6,936,454 B2 | | 8/2005 | Kelly et al. |
| 7,157,416 B2 | * | 1/2007 | Becker ............... C11D 3/38663 424/94.1 |
| 8,183,184 B2 | | 5/2012 | Berkland et al. |
| 2010/0069266 A1 | | 3/2010 | Battistel et al. |
| 2010/0184630 A1 | * | 7/2010 | Sullivan ............... C09K 8/52 507/216 |

OTHER PUBLICATIONS

Sundarram, A, et al, alpha-amylase production and applications: a review, journal of applied and environmental microbiology, 2014, vol. 2, No. 4, 166-175.*

Tizon, Ruby, et al, Effects of pH on amylase, cellulase and protease of the Angelwing claim, Euro. J. Exp. Bio., 2012, 2 (6):2280-2285.*
Worthington Biochemical Corporation "Effects of pH (Introduction to Enzymes)", 2 pages, printed Mar. 15, 2017.*
Worthington Biochemical Corporation "Cholesterol Esterase", 3 pages, printed Mar. 15, 2017.*
Nielsen et al. (2003) Biochem. J. 373:337-343 "Effect of Calcium Ions on the Irreversible Denaturation of a Recombinant Bacillus halmapalus a-Amylase: A Calometric Investigation".
Samborska (2007) Acta Agrophysica 9(1):233-244 "Enhancement of Thermal Stability of Aspergillus Oryzae Alpha-Amylase Using Stabilizing Additives".
Siddiqui et al. (2006) Society of Petroleum Engineers: SPE Europe/EAGE Annual Conference and Exhibition, Jun. 12-15, Vienna, Austria, Conference Paper "Evaluation of Acid Precursor-Enzyme System for Filter Cake Removal by a Single Stage Treatment".
Yadav and Prakash (2009) Journal of Biosciences 34(3):377-387 "Thermal Stability of Alpha-Amylase in Aqueous Cosolvent Systems".
Sharma et al. "Microbial acid-stable α-amylases: Characteristics, genetic engineering and applications", Process Biochemistry 48(2):201-211, Feb. 2013, retrieved from https://www.researchgate.net/publication/257538537_Microbial_acid-stable_a-amylases on Oct. 20, 2016. Abstract Only.
Xu et al. "Improving the acidic stability of a β-mannanase from *Bacillus subtilis* by site-directed mutagenesis", Process Biochemistry, Bolume 48, Issue 8, Aug. 2013, pp. 1166-1173, retrieved from http://www.sciencedirect.com/science/article/pii/S1359511313002845 on Oct. 20, 2016. Abstract Only.
Siddiqui et al. "Evaluation of Acid Precursor-Enzyme System for Filter-Cake Removal by a Single-Stage Treatment", SPE 99799, Paper was prepared for presentation at the SPE Europec/EAGE Annual Conference and Exhibition held in Vienna, Austria, Jun. 12-25, 2006, 13 pages.
Harris et al., "Effective water-based drill-in fluid filter cake cleanup by treatment fluids containing organic acid precursors", Cleansorb the Uniform Effect, White paper, Aug. 2014, 15 pages.

* cited by examiner

STABILIZED ACID PRECURSOR AND ACID-ENZYME FORMULATIONS FOR DRILLING MUD CAKE REMOVAL

TECHNICAL FIELD

The present invention relates to conformational stability of enzyme protein and in particular, to method in preserving the shelf life and enzymatic activity of enzyme formulations containing in-situ acid precursors used in drilling mud cake removal.

BACKGROUND

For horizontal wells drilled with water based mud system, the bio-polymeric drilling fluid form a strong and nearly impermeable mud cake coating on the wellbore wall, removal of which is of utmost importance to restore the productivity or injectivity of the well. An enzyme and a weak acid system attacks the bio-polymers and carbonate bridging material of the cake, resulting degradation of the filtercake, though stability of such enzyme in presence of a weak acid or an acid precursor releasing weak acid, has been a problem area.

The present invention is directed toward overcoming one or more of the problems discussed above.

DESCRIPTION OF THE PRIOR ART

Enzyme stabilization in the presence of functionally vital formulation constituents has gained notable significance owing to increasing number of its specialized applications. The stabilization of enzyme formulation during long-term storage conditions in presence of critically functional ingredients for specialized application poses a big obstacle in current science. A well-known drawback of designed enzyme formulations for special use is their relatively low activity on long-term storage.

U.S. Pat. No. 5,678,632, Moses, V. and Harris, R. E., 1997; U.S. Pat. No. 6,702,023, Harris, R. E. et al., 2004; U.S. Pat. No. 6,763,888 Harris, R. E. et al., 2004 and Siddiqui, M. A. et al., 2006 described the method of freshly preparing enzyme product containing in-situ acid precursors, where in-situ acid precursors compound are mixed with enzyme and brine for the filter cake removal in the oil and gas field application. Each of the patents and patent applications described herein, including U.S. Pat. Nos. 5,678,632, 6,702,023 and 6,763,888, are incorporated by reference herein in their entireties.

However, the long-term stability of enzyme formulations containing in-situ acid precursors has not been discussed in any prior art, where a particular difficulty has been the rapid decrease of enzyme activity in the formulation during normal storage conditions by the slow or fast hydrolysis of ester in the presence or absence of ester catalyst to generate organic acid, which perturbs the pH condition (alters electrostatic interactions between charged amino acids) and hinders the stability of the enzyme formulation. These electrostatic interactions are dependent on pKa values of amino acid side chains, which play a significant role in defining the pH-dependent traits of enzyme stability. Until now no such formulation has been able to rectify this difficulty and we are not aware of any prior art dealing with this problem. To the surprise of the inventors, this difficulty has been largely resolved by the inclusion of unique enzyme stabilizing ingredients such as metal halide salts and pH control additives in combination with a water activity reducing agent.

U.S. Pat. No. 7,157,416, Becker, N. T. et al., 2007, describes a method for enzyme-containing formulations having improved stability and enzymatic activity in liquid medium with inorganic salts in combination with a water activity reducing agent or polyol. Samborska, K., 2007, describes the method of stabilizing amylase with a water activity reducing agent. Another method for increasing the stability of amylase has been disclosed in the literature, which improves the storability of amylase by using a formulation comprising a water activity reducing agent and or inorganic salts (Nielsen, A. D. et al., 2003 and Yadav, J. K. and Prakash, V. 2009).

A water activity reducing agent alone or in combination with metal halide salts has been shown to offer greater conformational stability of enzymes against various degradation mechanisms and also protected specific enzyme activity to a great extent. However, no work has been cited which shows how a biopolymer degrading enzyme which has been formulated with an in-situ acid generated precursor can be protected against loss of enzyme activity in this type of formulation containing in-situ acid generating precursor, to be stable for long period on the shelf.

The shelf stability of in-situ acid-precursor enzyme formulations has not been discussed in the prior art and until now no stabilizers have been used to preserve the activity and shelf stability of a formulation containing both these components. We are not aware of any disclosure whatsoever wherein the use of metal halide salts and pH control additives alone or in combination with a water activity reducing agent has been taught, revealed or proposed for improving or enhancing the shelf stability of in-situ acid-precursor enzyme formulation, where in-situ acid-precursor are mainly ester compounds that dissociate by slow hydrolysis to generate organic acid, destabilize the enzyme by shifting the pH of the formulation outside the pKa of the enzyme protein and bring ionic disturbances during transport and long-term storage conditions. In view of the above, substantial efforts have been made to improve the stability of the enzyme formulation, so as to shield the enzymatic activity during transport and long-term storage. Clearly, there is a need for a novel enzyme formulation that contains in-situ acid precursor system, which is stabilized and exhibit high activity over a period of time and can be stored as a ready to pump formulation after diluting with sea water, brine or fresh water. The present invention provides a method of and compositions for increasing the stability of an in-situ acid-precursor enzyme formulation.

SUMMARY OF THE INVENTION

The present invention provides a method for improving the shelf life and preserving the enzymatic activity of the novel in-situ acid-precursor enzyme formulation during long-term storage conditions. It has been revealed that the high concentration of metal halide salts, such as sodium chloride (at least 1% to 10% w/w or higher), calcium chloride (at least 0.5% to 10% w/w or higher) and pH control additives, such as sodium ethanoate (at least 1% to 10% w/w or higher) in combination with a water activity reducing agent, such as saccharose (1% to 30% w/w or higher), provides a high degree of stability for enzyme formulation containing in-situ acid precursor system. These in-situ acid precursors (mainly ester compounds) such as ethylene glycol diacetate, dissociate by slow hydrolysis to generate organic acid (acetic acid) during normal storage condition.

Another feature of the present invention provides a novel formulation providing an in-situ acid-precursor enzyme-stabilizing environment. In one embodiment, the novel in-situ acid-precursor enzyme formulation includes one or more enzymes, a high concentration of metal halide salts and pH control additives in combination with a water activity reducing agent.

DETAILED DESCRIPTION OF THE INVENTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

As discussed above, the subject of the instant invention are enzymes that are formulated according to methods known in the art with in-situ acid precursors for use in treating damage caused by combinations of both acid soluble material and polymers in filter cakes, in one single fluid. In particular the method provides a single stage treatment capable of completely removing filter cake damage caused by those drilling fluids containing carbonate as a fluid loss material and polymers.

The present invention provides a method for improving the shelf life and preserving the enzymatic activity of an in-situ acid-precursor enzyme formulation during long-term storage conditions. This method of invention fortifies and stabilizes hydrolase enzymes when formulated with acid precursors, enabling them to retain their activity during transport and long-term storage conditions. Generally, this result is achieved by the inventor's inclusion of metal halide salts and pH control additives in combination with water reducing activity agent. The inventors hereof have determined that the high concentration of metal halide salts (e.g., sodium chloride, calcium chloride) and pH control additives (e.g., sodium ethanoate) in combination with a water activity reducing agent (e.g., a saccharose) provides a high degree of shelf stability of in-situ acid-precursor enzyme formulation during long-term storage conditions.

Thus, as detailed above present invention is directed towards improving or enhancing the shelf stability of in-situ acid-precursor enzyme formulations, where in-situ acid-precursor are mainly ester compounds that dissociate by slow hydrolysis to generate organic acid. The acid precursor (as discussed more fully hereinbelow) may also include the organic acid. However, inclusion of acid precursors or weak acids tends to destabilize the enzyme by shifting the pH of the formulation outside the pKa of the enzyme protein and bring ionic disturbances during transport and long-term storage conditions. In view of the above, the present invention is useful to improve the stability of the enzyme formulation, so as to shield the enzymatic activity during transport and long-term storage. Thus, the present invention provides a novel enzyme formulation that contains in-situ acid precursor system, comprising further ingredients which function to stabilize the enzyme and in-situ acid precursor formulation. This stabilized composition exhibits high activity over a period of time and can be stored as a ready to pump formulation after diluting with sea water, brine or fresh water. The present invention is directed towards the discovery that an inclusion of metal halide salts and pH control additives in combination with a water activity reducing agent has significantly improved the shelf stability of enzyme formulation comprising in-situ acid precursors on long-term storage.

Accordingly, the invention is directed to compositions and methods for stabilizing a composition comprising enzymes which have been formulated with in-situ acid precursors. A composition comprising enzymes which have been formulated with in-situ acid precursors is referred to variously herein as an enzyme formulation comprising in-situ acid precursors, in-situ acid-precursor enzyme formulation.

The composition comprising an enzyme which has been formulated with an in-situ acid precursor includes at least two components: the enzyme and the in-situ acid precursor.

A suitable enzyme for the composition comprising an enzyme which has been formulated with an in-situ acid precursor includes a hydrolase. Generally, a disadvantage of most commercially designed enzyme formulations is their shelf stability on transport and storability. They generally degrade in extreme conditions and are inactivated rapidly by heat and other environmental modifications such as changes in pH that result in electrostatic interactions between charged amino acids. These electrostatic interactions are dependent on pKa values of amino acid side chains, influence ionization equilibria of acidic and basic groups and alter their pKa values, which play an important role in defining the pH-dependent characteristics of enzyme stability. Enzymes being amphoteric molecules have a number of discrete benefits over conventional chemical catalysts. They contain a large number of acid as well as basic groups on their surface. Acid dissociation constant also known as acidity constant or acid-ionization constant (pKa) and pH play a crucial role in enzyme stability. The charges on enzymes will differ, depending to their pKa and the pH of their environment. This will affect the total net charge of the enzymes, distribution of charge on their exterior surfaces and also the reactivity of the catalytically active groups. Taken together, the changes in pH alter the activity, structural stability and solubility of the enzyme.

Generally, enzymes suitable for this invention are those that are selected on the basis of their ability to hydrolyse the biopolymer components that are believed to contribute to the damage caused by water based drilling fluid in sub terrain formations. Suitable examples of enzymes which may be used to break polymers include enzymes which can hydrolyse starch, xanthan, cellulose and guar or derivatives of these biopolymers that are used as bridging material of drilling fluid in oil and gas field applications, such as industrial gums such as those generally classified as exudate gums, seaweed gums, seed gums, microbial polysaccharides, and hemicelluloses (cell wall polysaccharides found in land plants) other than cellulose and pectins. Examples include xylan, mannan, galactan, L-arabino-xylans, L-arabino-D-glucurono-D-xylans, D-gluco-D-mannans, D-galacto-D-mannans, arabino-D-galactans, algins such as sodium alginate, carrageenin, fucordan, laminarin, agar, gum arabic, gum ghatti, karaya gum, tamarind gum, tragacanth gum, locust bean gum, cellulose derivative such as hydroxyethylcellulose or hydroxypropylcellulose, and the like and hydratable polysaccharides having galactose and/or mannose monosaccharide components, examples of which include the galactomannan gums, guar gum and derivatized guar gum.

Patent literature relating to polysaccharide degradation by enzymes in oil and gas field applications can be found in U.S. Pat. Nos. 6,110,875, 6,936,454, 4,284,722, 5,126,051, 8,183,184, 5,441,109, U.S. Patent Publication 2010/0069266, U.S. Pat. Nos. 5,224,544, 5,566,759, 4,682,654, 5,881,813, 5,067,566, 5,547,026, and 6,794,340, each of which is incorporated herein by reference in its entirety. Usually, one or more enzymes may be included in the novel formulations of the present invention.

Thus, enzymes suitable for the present invention include, without limitation, a hydrolase. A hydrolase is an enzyme that catalyzes the hydrolysis of several types of compounds. In particular, a hydrolase useful for the present invention includes glycosidases which sever bonds between sugar molecules in carbohydrates. A preferred polymer breaking enzyme used in the present invention includes a hydrolase, similar to the polysaccharide degrading enzymes known to be useful to hydrolyse polysaccharides, to reduce the viscosity of polysaccharide thickened compositions and to disrupt filter cakes in oil gas field applications.

In one embodiment, the hydrolase is a glycosylase, such as, for example, α-amylase, β-amylase, xanthanase enzyme complex, galactosidase, mannanase, amyloglucosidase, invertase, maltase, pectinase, hemicellulose, endoamylase, galactomannase, cellulose, and the like.

In one embodiment, the polymer breaking enzyme is an alpha amylase (or α-amylase), that hydrolyses alpha-1,4 bonds of large polysaccharides (starch and glycogen), resulting the smaller by-products of glucose and maltose. Amylose (a single straight chain starch) is a polymer of alpha glucose that only has glycosidic bonds between C1 of one glucose and C4 of the other, whereas amylopectin is a branched chain of alpha glucose, which has C1:C6 glycosidic bonds as well as C1:C4 glycosidic bonds. The amount of enzyme to use in the formulations is any amount that is effective for drilling mud cake removal, as is known in the art and disclosed in any of the patents and patent applications incorporated herein by reference.

Preferred in-situ acid precursors used in the present invention are mainly carboxylic acid ester compounds that dissociate by hydrolysis at high temperature to produce organic acid. See, for example, U.S. Pat. No. 6,763,888. The rate of the reaction for these esters increases as the temperature increases to produce an organic acid. The in-situ acid precursor's incorporation into enzyme formulation is preferably those which can effectively breakdown the biopolymer damage or filter, but with low toxicity, high flash point and high environmental acceptability. The concentration of in-situ acid precursors incorporated into the formulations of the present invention will typically be at least 1% w/w but may be up to 20% w/w or higher. In general it has been found that 5% to 10% w/w ester when used in combination with a suitable hydrolase enzyme alone or in combination of enzymes will be used. See U.S. Pat. No. 6,763,888.

Examples of in-situ acid precursors include those that hydrolyze to produce organic acid, generally an aliphatic carboxylic acid. In another embodiment, the in-situ precursor is the organic acid itself. Preferably the acid is of formula $RCO_2H$ wherein R is hydrogen, an alkyl group having from 1 to 6 carbon atoms or —R'—$CO_2H$ where R' is a bond or an alkylene group having from 1 to 6 carbon atoms, the said alkyl or alkylene group being unsubstituted or substituted by halogen or hydroxy. Examples include 1,2,3,-propanetriol triacetate, 1,2,3,-propanetriol diacetate, ethylene glycol diacetate, diethylene glycol diacetate or triethylene glycol diacetate. Where the acid has a hydroxy substituent, the ester may be a cyclic ester such as a lactone. The alcohol portion of the ester may be monohydric or polyhydric as long as the esters are sufficiently water soluble at formation temperatures. Partial esters of the polyhydric alcohols can be used in which case the unesterified hydroxyl groups serve to increase the water solubility of the ester.

In one embodiment, the esters are acetic esters of 1,2,3-propanetriol (glycerol) and 1,2-ethanediol (ethylene glycol). Suitable esters include ethylene glycol diacetate, 1,2,3-propanetriol triacetate, 1,2,3-propanetriol diacetate, diethylene glycol diacetate, triethylene glycol diacetate, ethyl acetate, ethyl lactate, methyl acetate, ethyl formate or methyl formate, or the acids of the above. The resultant acids and/or the acid precursor include formic acid (esters of formic acid), acetic acid (esters of acetic acid), and lactic acid (esters of lactic acid).

In the compositions comprising the invention, the in-situ acid-precursor enzyme formulation includes further components in order to enhance stability of the in-situ acid-precursor enzyme formulation. The further components include a water activity reducing agent, a metal halide salt, a calcium salt, and a pH control additive.

Generally, compositions of the present invention include a water activity reducing agent, such as a saccharose (1% to 30% w/w or higher), high concentration of metal halide salts (at least 1% to 10% w/w or higher), calcium salt (at least 0.5% to 10% w/w or higher) and pH control additives, such as sodium ethanoate (at least 1% to 10% w/w or higher), as explained in more detail below.

The method of protein stabilization in the in-situ acid precursor enzyme formulation includes the presence of a water activity reducing agent. Water activity is defined as the qualitative measurement of water's energy state in a given system based on thermodynamics and physical-chemical properties. The water activity of a given material depends on the ionic binding, dipolar forces, van der Waals force, hydroxyl groups in sugars, carbonyl and amino groups in proteins etc. These agents in the enzyme formulation strengthen the hydrophobic interactions among non-polar amino acid residues. These interactions, in addition to hydrogen bonds, ionic bonding and van der Waals interactions are essential to sustain the native catalytic structure of the enzyme. The interactions between protein, solvent and co-solvent can be expressed in terms of a variety of thermodynamic and preferential interaction parameters. The protein surface, being heterogeneous in nature can prominently influence solvent structure and the distribution of co-solvents. The extent of protein stabilization in different denaturing states is mostly depends upon the quality of the co-solvent, its association with water and nature of the protein. These interactions make a protein macromolecule more rigid and therefore more resistant to heat unfolding. The presence of these agents in enzyme solution brings about changes in physicochemical properties of the protein mainly by altering solvent/water structure resulting in protein stabilization.

Suitable water activity reducing agents include any agents that increase the order of water, e.g., exhibiting stronger interactions with water molecules than water with itself and therefore capable of breaking water-water hydrogen bonds, thus remaining hydrated. Such water activity agents include any polyhydroxy compounds. Suitable polyhydroxy compounds include sugars and sugar alcohols. Examples of such compounds include saccharose, which is a disaccharide of glucose and fructose with an alpha 1, 2 glycosidic linkage, sorbitol, mannitol, glycerol, trehalose, propylene glycol, and combinations thereof. Amounts to use include at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, or at least about 50%, w/w. In other embodiments, amounts to use include from about 1% to 50% w/w, from about 1% to about 30% w/w, from about 5% to about 30% w/w, from about 10% to about 25% w/w, from about 15% to about 20% w/w).

The compositions and methods of stabilization for the in-situ acid precursor enzyme formulation also include the presence of metal halide salt. According to the allosteric phenomenon, the catalytic powers of active sites of enzymes are often influenced by ligands and ions. Enzymes are significantly stabilized by anions that readily bind to their binding site causing a significant increase in the amylase-$Ca^{2+}$ binding constant and therefore, prevent the dissociation of calcium ions and thereby stabilize the enzyme. Enzymes have a binding site for chloride ion, which has a positively charged amino acid residue. In addition to the anion, amount of enzyme stabilization is also influenced by both salt concentration and the type of cation involved. The chloride ions fit into the anionic binding site causing a conformational change resulting in enzymatic stabilization. In solution, NaCl dissociates into $Na^+$ and $Cl^-$ ions which plays a pivotal role to stabilize the exposed hydrophilic residues of the protein. This leads to active folding of the enzyme under variable ionic strength conditions. Furthermore, the chloride ions that come from sodium chloride provide significant enzyme stabilization by suppressing the metal ion dissociation resulting in increased enzyme stability.

Suitable metal halides for the invention include sodium chloride, calcium chloride and/or potassium chloride. A sodium halide salt may be used at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30% w/w. Where the metal halide is calcium chloride, amounts to use include at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30% w/w.

Where the enzyme is α-amylase, the amylase is a metalloenzyme that requires calcium ions for its activity. Therefore in embodiments where α-amylase is used, the composition further comprises a source of calcium ions. Suitable sources of calcium ions for activity of α-amylase are known in the art, and include calcium chloride. Suitable amounts of calcium ions to include are also known in the art, and include, for example, at least about 0.5% w/w of calcium chloride, for example, in a composition comprising α-amylase.

The compositions and methods of the present invention further comprise a pH control additive. The role of pH control additives such as sodium ethanoate is very critical to act as conjugate base of an organic acid, generated by the slow hydrolysis of an ester present in the enzyme formulation. A suitable pH control agent includes the conjugate base of an acid of an in-situ acid precursor, as disclosed hereinabove. This acts as a buffer by maintaining the hydrogen ion concentration to keep a relatively constant pH (near the pKa value of amino acid) and preserving the required activity of the enzyme during long-term storage condition. The change in pH of enzyme formulation can affect the state of ionization of acidic (carboxyl functional groups in their side chains) or basic amino acids (amine functional groups in their side chains), and induces change in the number of protons bound to the native and unfolded states of the protein, leading to the distorted protein recognition or an enzyme inactivation. The addition of pH control additives will cause corresponding changes in the concentration of acetic acid released by an ester and acetate ion by maintaining hydrogen ion concentration in the enzyme formulation. The pH control additives used to formulate proteins and show little or no changes in pH, also exhibits insignificant diffusion through biological membranes, and have highest buffer capacity at a pH (pKa values of amino acid) where the protein exhibits optimal stability. The pKa values of the active-site residues in an enzyme are essential to hold the activity of the enzyme. Hence, the pKa values of the ionizable residues are the source for understanding the pH-dependent specialty of proteins and catalytic mechanisms of enzymes. The presence of salts along with pH control additives can influence protein conformation to the degree that anions or cations of the salt could possibly converted into buffer components. As the concentration of salt is more than that of buffer, it turns out to be the effective buffer in the reaction.

Effective pH control agents for the invention include any salt of a weak acid capable of acting as part of a buffering system. A suitable salt includes sodium ethanoate; other suitable salts include sodium citrate, potassium phosphate and the like. Amounts to use include at least about amounts to use include at least about 0.5%, at least about 1%, at least about 2%, at least about 3%, at least about 4%, at least about 5%, at least about 6%, at least about 7%, at least about 8%, at least about 9%, at least about 10% w/w. In one embodiment, the amount to use is between about 2% and about 3% w/w.

Taken together on the basis of invention, it appears that the presence of metal halide salts and pH control additives in combination with a water activity reducing agent plays an important role in enzyme stabilization in the presence of an in-situ acid precursor during long-term storage condition.

The stabilized in-situ acid precursor enzyme formulation in the present invention is stable during long term storage and transport. This formulation can be applied in oil and gas fields, where they allow a dual attack by acting synergistically on the carbonate or acid soluble material and polymer components of filter cakes in a single stage treatment.

In-situ acid precursor enzyme formulations of the present invention are mainly efficient in stabilizing enzymes during long-term storage conditions, over a wide range of temperature conditions, including those which are above standard enzyme storage conditions of 4° C. For example, compositions of the present invention are stabilized in temperature range from 25 to 55° C., for example, and/or at room temperature (20-30° C.).

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The following methods are provided for illustrative purposes only and are not intended to limit the scope of the invention.

Example 1

Figure 5:
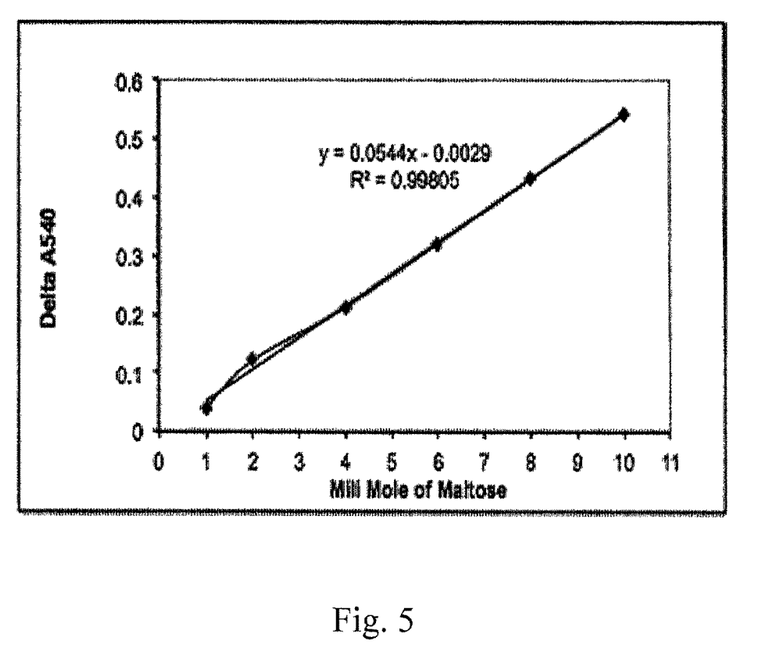
FIG. 5 shows a range of color development in a maltose assay in accordance with the amount of maltose generated.

The method of invention for the formulation generally involves the following: (1% to 30% w/w) saccharose, (1% to 10% w/w) sodium chloride or mixtures of sodium chloride and sodium ethanoate, (0.5% to 10% w/w) $CaCl_2$ reagent was mixed followed by adding up the selected enzyme. Initial Enzyme dilution: Added 250 µl of enzyme sample to 12.25 ml 0.02 M sodium phosphate buffer. Further dilutions: Prepared serial dilutions of each sample by adding 250 µl of previous dilution to 2.25 ml of 0.02M sodium phosphate buffer. This dilution was done (with known dilution factor) in a manner, when the hydrolization product (maltose in this case) would produce color with DNS, absorbance upon incubation would fall within the stipulated range, as seen in FIG. 5.

According to the Lambert-Beer law, there is a linearity between activity and absorbance within this absorbance range and the Maltose standard curve is used to back calculate the amount of Maltose released, using the color (OD-Delta Absorbance). The resulting mixture was allowed to dissolve in water at room temperature. The chosen salt concentration was prepared by suspending the salt (1% to 10% w/w) sodium ethanoate before adding to the dissolved enzyme. Next, (1% to 20% w/w) ethylene glycol diacetate was supplemented to the enzyme salt mixture and the ensuing solution was mixed at room temperature (25° C.) for approximately 2 hours. Next, the in-situ acid precursor enzyme formulation was filtered and the ensuing solution was stored and tested for the stability studies set out below.

Method 1: Activity levels for all of the above enzyme formulations were checked as shown by the data of Method 1, which demonstrates that 10% w/w sodium chloride, 0.5% w/w calcium chloride in combination with 30% w/w saccharose is an effective stabilization agent for an in-situ acid precursor enzyme formulation. Activity retention of enzyme formulation at 120 days (4 months) by using the three stabilizers was shown between 85% or above as compared to only 50% in the formulation (Control) that did not include saccharose, sodium chloride and/or sodium ethanoate at room temperature (25° C.).

Method 2: 8% w/w sodium chloride, 2% w/w sodium ethanoate and 0.5% w/w calcium chloride in combination with saccharose for an in-situ acid precursor enzyme formulation exhibited high stability (over 95% activity retention after 30 days and 90% after 60 days at room temperature. The data further reveals that the higher level of enzymatic activity (at least 90%) retained by the inclusion of enzyme stabilizers up to 120 days (4 months).

Method 3: 7% sodium chloride, 3% sodium ethanoate and 0.5% calcium chloride in combination with saccharose for in-situ acid precursor enzyme formulation exhibited high stability (greater than 95% activity retention after 30 days and 92% after 60 days at room temperature. The data further reveals that the higher level of enzymatic activity (at least 90%) retained by the inclusion of enzyme stabilizers up to 120 days (4 months).

TABLE 1

Method for the composition of in-situ acid precursor enzyme formulation

| Description | Enzyme (% w/w) | Saccharose (% w/w) | NaCl (% w/w) | NaOAc (% w/w) | $CaCl_2$ (% w/w) | In-situ acid precursor (% w/w) | DM water |
|---|---|---|---|---|---|---|---|
| Control | 40 | Nil | Nil | Nil | Nil | 7 | 53% |
| Method 1 | 40 | 30 | 10 | Nil | 0.5 | 7 | 12.5% |
| Method 2 | 40 | 30 | 8 | 2 | 0.5 | 7 | 12.5% |
| Method 3 | 40 | 30 | 7 | 3 | 0.5 | 7 | 12.5% |

Methodology of amylase assay/preparation of maltose standard: In numbered tubes, prepare 5 maltose dilutions ranging from 1 mM to 10 mM. Use distilled water as blank. Into a series of corresponding numbered tubes, pipette 1 ml of each dilution of maltose. Add 1.2 ml 3,5-dinitrosalicylic acid (DNS) solution to each tube. Let it stand at room temperature for 15 min. Incubate at 95° C. in a water bath for 5 min and cool in a room temperature water bath for 10 min. Transfer to a test tube stand and incubate for 10 min at room temperature. Take 200 µl of the reaction mixture and dilute with 3 ml distilled water in a cuvette. Mix and read at 540 nm.

Assay Procedure: Equilibrate 0.50 ml of the 1.2% starch substrate at 90° C. in covered glass test tubes for 10 min each. At exactly 10 min, at timed intervals of 20 seconds (start timer), rapidly add 0.5 ml of the prepared enzyme dilution to the equilibrated starch substrate. Recap, vortex and incubate at 90° C. for exactly 10 min. Twenty (20) seconds later, prepare the second tube and then continue in the same manner with the rest of the tubes.

After exactly 10 min, add 1.2 ml of DNS-solution, recap and vortex. Allow this solution to stand at room temperature for 15 min. Cover the tubes with rubber stoppers or plastic caps to prevent evaporation. Incubate for 5 min in a water bath at 95° C. with respective controls. After boiling, cool down the samples for 10 min in a water bath at room temperature, then let sit at room temperature for 10 min. Measure the absorbance of the enzyme samples at 540 nm against distilled water blank and rate of the appearance of reducing sugar is a measure of amylase activity.

Run one enzyme blank for each sample in the assay. Incubate 0.5 ml of starch substrate at 90° C. for 10 min in glass test tubes. Add 1.2 ml of DNS solution and 0.5 ml of a suitable enzyme dilution (same as above). Allow this solution to stand at room temperature for 15 min. Cover tubes to prevent evaporation. Boil for 5 min in a boiling bath. Measure the absorbance of the enzyme blanks at 540 nm against distilled water blank.

Example 2

Figure 1:
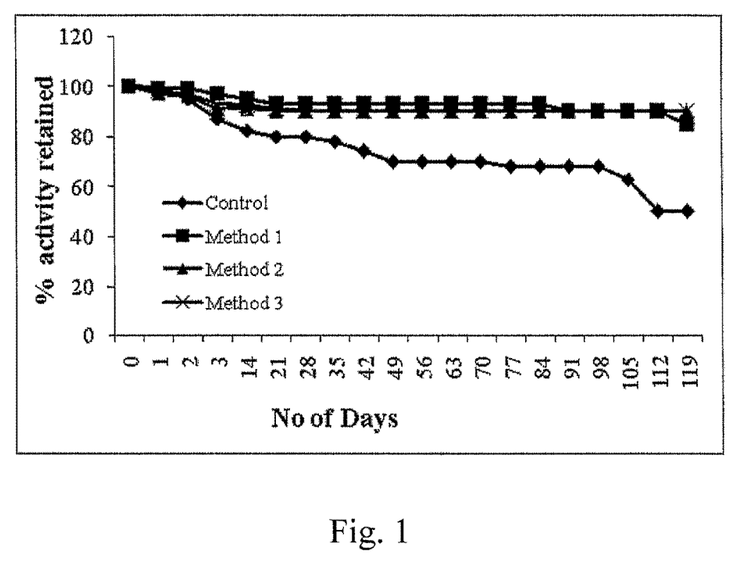
FIG. 1 is the stabilization effect of different composition of stabilizers on in-situ acid precursor enzyme formulation.
Figure 2:
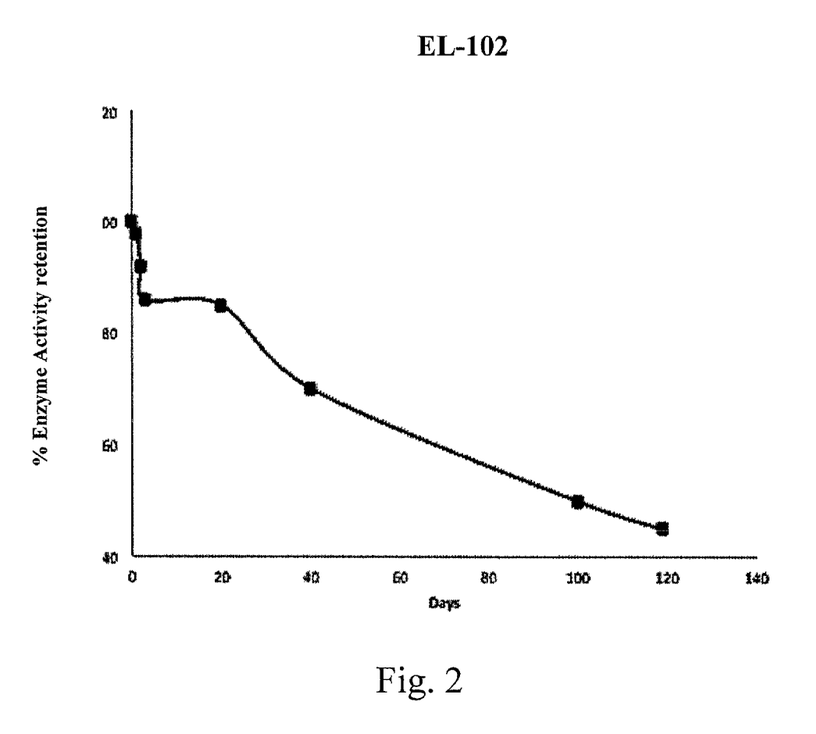
FIG. 2 is the stabilization effect of E102 formulation of different composition of stabilizers on in-situ acid precursor enzyme formulation.
Figure 3:
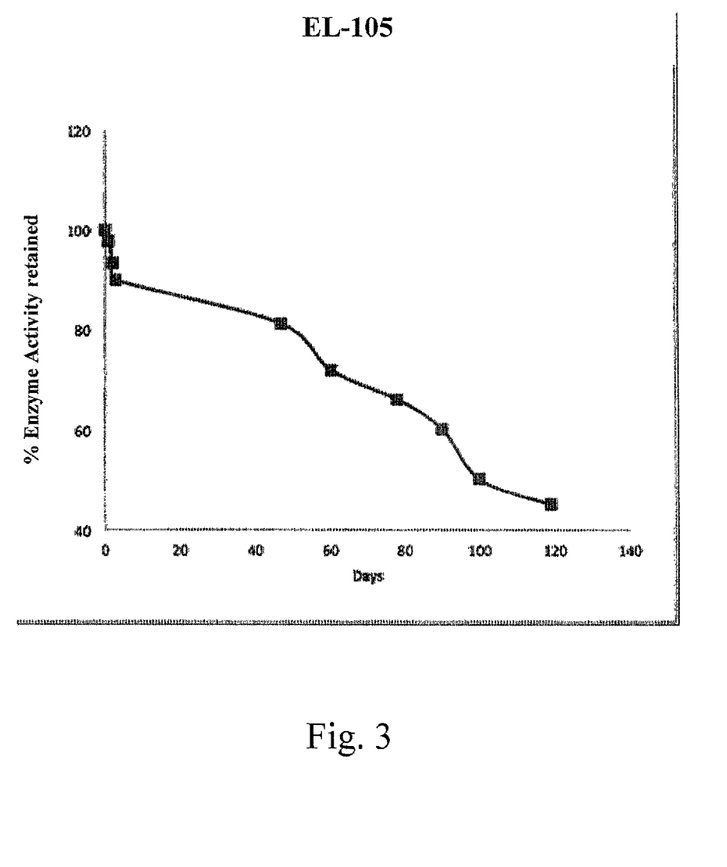
FIG. 3 is the stabilization effect of E105 formulation of different composition of stabilizers on in-situ acid precursor enzyme formulation.
Figure 4:
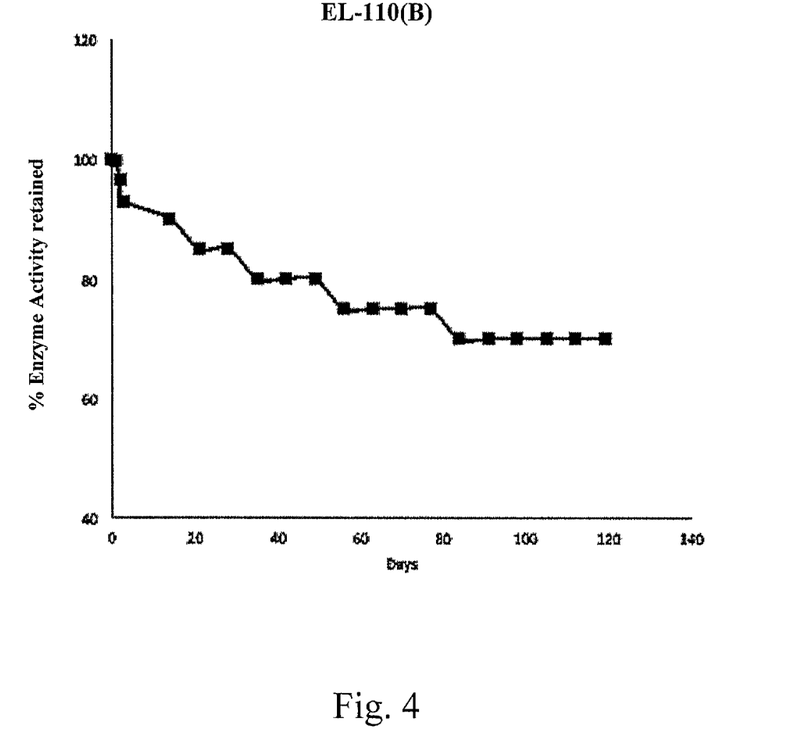
FIG. 4 is the stabilization effect of E110(B) formulation of different composition of stabilizers on in-situ acid precursor enzyme formulation.

This example uses the same conditions as discussed above for Example 2. However, this Example is illustrative of results for stability when using industry standards for stabilizing enzymes, and shows that industry standard methods for preserving enzyme activity do not result in retaining acceptable stability levels. See FIGS. 2-4.

only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method for stabilizing a hydrolase enzyme in the presence of an in-situ acid-precursor, comprising:
    adding to the enzyme and in-situ acid precursor an effective amount of (1) sodium chloride having a concentration of between from about 7% to 8% w/w of the composition, (2) a pH control additive comprising sodium acetate having a concentration of between from about 2% to about 3% w/w of the composition, (3) calcium chloride having a concentration of at least about 0.5% w/w of the composition, and (4) a water activity reducing agent comprising sucrose having a concentration of about 30% w/w of the composition, and
    storing the enzyme and in-situ acid precursor at a temperature between 25 to 55° C.,
    wherein at least 90% of the original enzyme activity remains after 120 days storage room temperature outside of a wellbore, wherein the hydrolase enzyme is selected from the group consisting of an amylase, a cellulase, a hemicellulase, a mannanase, a galactomannanase, and combinations thereof, and
    wherein the in-situ acid-precursor is ethylene glycol diacetate and has a concentration of between from about 5% to 10% w/w of the composition, and wherein the enzyme has a concentration of about 40% w/w.

2. The method of claim 1, wherein the amylase is an alpha amylase enzyme that catalyses the hydrolysis of alpha bonds of large, alpha-linked polysaccharides such as starch and glycogen, yielding glucose and maltose.

3. The method of claim 2, wherein said alpha amylase is sourced either from bacterial or fungal species.

4. A composition for stabilizing a hydrolase enzyme in the presence of an in-situ acid-precursor, wherein the composition comprises the in-situ acid precursor ethylene glycol diacetate having a concentration of between from about 5% to 10% w/w of the composition, the hydrolase enzyme, sodium chloride having a concentration of between from

TABLE 2

Method for the composition of in-situ acid precursor enzyme formulation

| Description | Enzyme (% w/w) | Sorbitol (% w/w) | NaCl (% w/w) | NaOAc (% w/w) | CaCl$_2$ (% w/w) | In-situ acid precursor (% w/w), i.e., Ethylene glycol diacetate | DM water |
|---|---|---|---|---|---|---|---|
| EL-102 | 40 | 8 | Nil | Nil | Nil | 7 | 53% |
| EL-105 | 40 | 20 | Nil | Nil | 4 | 7 | 12.5% |
| EL-110(B) | 40 | 30* | Nil | Nil | 0.5 | 7 | 12.5% |

*sucrose

The description of the present invention has been presented for purposes of illustration and description, but is not intended to be exhaustive or limiting of the invention to the form disclosed. The scope of the present invention is limited about 7% to 8% w/w of the composition, calcium chloride having a concentration of at least about 0.5% w/w of the composition, a pH control additive comprising sodium acetate having a concentration of between from about 2% to about 3% w/w of the composition, and a water activity reducing agent comprising sucrose having a concentration of about 30% w/w of the composition, and wherein the composition retains at least 90% of the original enzyme activity after 120 days storage at room temperature outside of a wellbore, and wherein the enzyme has a concentration of about 40% w/w.

\* \* \* \* \*